United States Patent [19]

Conover

[11] 4,444,662
[45] Apr. 24, 1984

[54] MICROPOROUS LAMINATE

[75] Inventor: Stephen P. Conover, Minneapolis, Minn.

[73] Assignee: Applied Membrane Technology, Inc., Minnetonka, Minn.

[21] Appl. No.: 87,227

[22] Filed: Oct. 22, 1979

[51] Int. Cl.³ .............................................. B01D 31/00
[52] U.S. Cl. .................................... 210/500.2; 55/16; 55/158; 422/48
[58] Field of Search .......................... 428/304; 427/245; 210/500 M; 525/906; 55/16, 158; 128/1 R; 422/48

[56] References Cited

U.S. PATENT DOCUMENTS

| | | | |
|---|---|---|---|
| 3,539,657 | 11/1970 | Noshay et al. | 525/906 X |
| 3,767,737 | 10/1973 | Lundstrum | 55/158 X |
| 4,008,047 | 2/1977 | Peterson | 210/500 M X |

Primary Examiner—Frank A. Spear, Jr.
Attorney, Agent, or Firm—James R. Cwayna

[57] ABSTRACT

A laminate formed by the solvent casting of a two phase siloxane-polyarylene polyether block copolymer onto a suitable microporous substrate such as a microporous polypropylene film, to produce a gas permeable and blood compatible membrane having sufficient mechanical strength for use in blood oxygenators and gas separation devices. For use in blood oxygenators, implantable biomedical devices, blood sampling, analysis or purification devices and artificial membrane lungs for cancer therapy or lung disease therapy, the two phase block copolymers such as polysufone-polydimethylsiloxane block copolymer preferably have molecular weights in the ratio 5,000/5,000 $M_n$'s with a 45% volume fraction as polysulfone, or at least 50% volume fraction represented as siloxane. For use in gas separation devices, the molecular weights of the polysulfone-polydimethylsiloxane blocks may be varied from 1,500 to 100,000 or greater $M_n$'s with 10 to 90% by weight siloxane, and from 90 to 10% by weight polysulfone, with a tensile modulus less than 100,000 psi and tensile elongation of at least 100%.

The process for producing the laminate consists of a meniscus dip coating technique to apply a uniform coating of the polymer to only one side of the microporous substrate in order to maintain coating thickness and to leave the other side uncoated for ease of heat sealing or potting of the membranes together into envelopes.

10 Claims, 3 Drawing Figures

MICROPOROUS LAMINATE

FIELD OF THE INVENTION

This invention relates generally to polymers that can be formed into films, membranes, coatings, fibers, woven and non-woven layers and similar structures, the structures having gas permeability, hydrolytic stability, mechanical strength and blood compatibility and more specifically to the novel formation of supported ultrathin membranes of these polymers to have hydrolytic stability over a wide range of pH, including blood pH of 7.4, and under sterilization conditions of, for example, 100° C. These ultrathin membranes may be used in devices wherein the blood of a living animal comes into contact with a non-living surface and include blood oxyhenators, biological implants, catheters, cannulas and other artificial organs, filters, probes and devices for sampling and analysis of blood as well as gas permeability devices.

BACKGROUND OF THE INVENTION AND PRIOR ART RELATED THERETO

The prior art recognizes the utilization of polymers that can be formed into films, membranes, coating, woven and non-woven layers and similar structures, which structures have blood compatibility, hydrolytic stability and gas permeability. Numerous types of gas permeable membranes for use in gas separation devices, blood-gas exchange devices and methods for preparation of these membranes also exists in the prior art.

Major prior art references related to the use of such polymers in association with blood analysis, sampling, gas exchanges and similar processes are as follows:

U.S. patent to R. J. Peterson entitled Blood Compatible Polymers for Blood Oxygenation Devices, U.S. Pat. No. 4,008,047, issued Feb. 15, 1977;

U.S. patent to Theodor Kolobow, entitled Blood Compatible-Gas Permeable Laminated Carbon Containing Silicone Rubber Membrane, U.S. Pat. No. 4,093,515, issued June 6, 1978;

U.S. patent, assigned to General Electric Co., entitled Organopolysiloxane-Polycarbonate Block Copolymers, U.S. Pat. No. 3,189,662; and, A publication "Interactions of Materials with Blood" entitled Blood Compatible Synthetic Polymers by S. D. Bruck published in 1974.

This latter publication provides a summary of the problems of bringing organic and inorganic foreign substances into contact with the blood of a living animal. Some of these problems include the loss of platelet preservation and activity and damage to proteins and cellular material in the blood.

The applicant has found that the membranes provided by these prior art membranes have been subject to various problems. Such problems include, but are not limited to the following: hydrolytic instability in the case of fluorinated ethylcellulose at pH levels of 9 and polyethylene-vinyl alcohol copolymers at pH levels of 7; inability to autoclave or sterilize satisfactorily in the case of organo-polysiloxane-polycarbonate block copolymers; carbon dioxide removal limitations in the cases of silicone rubber fabric reinforced silica filled membranes, fluorinated ethyl-cellulose organopolysiloxane-polycarbonates, polyfluoro-siloxane and laminated carbon containing silicon rubber membranes; relatively low gas permeabilities requiring larger than necessary surface areas for blood contact and gas exchange with all of the above; and hematological damage due to surface irregularities such as protruding silica crystals on the exposed surface of silicone rubber membranes and fluorosilicone silica reinforced membranes; and poor physical strength properties and high costs in the cases of polyalkylsulfones, polyfluorosiloxanes and the rest of the above.

Similarly, with other materials that have been used in the prior art, various problems exist. Gas transfer inadequacies and blood damaging characteristics occur with the use of uncoated microporous materials such as teflon, polypropylene and silicone hydrofugated polynosic fabric. The damaging characteristics are not due to poor gas transfer rates, but rather to a carbon dioxide flux decline over time due to water vapor condensation on the gas side micropores, and alternatively, the flooding of blood side micropores. This excessive water vapor loss is implicated in causing hyperosmolar states and, hypernatremia. This flux and condensation with uncoated microporous membranes requires the use of a heated and humidified gas supply in order to minimize these effects but the drawbacks limit the useful life of microporous membrane oxygenators to 6 to 8 hours and these are still implicated in causing deposition of blood-derived material.

It has now been found that the gas permeability, blood compatibility, hydrophobicity, ease of manufacture, mechanical strength, handling properties, hydrolytic stability and other desired properties for polymers used for gas permeable membranes or in the mentioned biological environs can be effectively combined in a composite membrane consisting of two phase siloxane-polyarylene polyether block copolymers cast upon and onto a microporous substrate. The use of ultrathin block copolymer membranes cast upon a microporous support material has not been recognized as having excellent utility in fields requiring blood compatibility or gas permeability.

SUMMARY OF THE INVENTION

The present invention provides the method and means for producing a laminate consisting of two phase siloxane-polyarylene polyether block copolymers, such as polysulfone-polydimethylsiloxane, solvent cast, via a meniscus dip coating method, onto microporous substrates, such a polypropylene film, CELGARD, a registered trademark of Celanese Plastics Co. meets these requirements.

Such a two phase block copolymer, as used in this invention, is film-forming and elastomeric and therefore ultrathin layers of these block copolymers can be obtained in the form of solvent cast films, membranes, coatings, etc.

For coatings on gas impermeable substrates, the coating thickness is not highly critical, and a coating of one mil or slightly less is adequate for continuous coverage. For purposes of blood oxygenation, thicknesses of about 0.5 mil, approximately 13 microns, or far less are preferred. The solvent casting methods employed by the applicant allow the manufacture of ultrathin films or membranes from 0.01 to 5.00 microns thick and such membranes are useful for blood oxygenating films or membranes and as gas separation membranes or films. The films, membranes and coatings made from these polymers can be in the form of coils, laminates, composites, hollow fibers or the like, or can be placed in rigid frames or folded parallel plate devices.

For gas exchange or separation applications, the thin membranes of the present invention must be placed in combination with a porous support membrane. This porous support membrane should have pores generally smaller than 5,000 angstroms and pores in the range of from 500–2,000 angstroms are preferred. The smaller pore structure is required for casting thin membranes as well as for operations at higher pressures. The thickness of the support membrane should be in the range of 1–20 mils with a preferred thickness of from 1–5 mils. Materials presently available that may serve as such support membranes include the Celgard microporous films identified as 2400, 2402, K-203, K-204, K-205 and 4410; microporous polysulfone films; other microporous materials with sufficiently smooth surfaces such as polycarbonate; and, microporous hollow fibers made from polypropylene and polysulfone.

The invention provides the apparatus for continuous manufacturing through utilization of a meniscus dip coating process. Microporous polypropylene material, as described, is provided in roll form and is unrolled or removed therefrom and passed through the coating apparatus in a manner to coat only one surface thereof with the polysulfone-polydimethylsiloxane solution, then dried and wound onto a roll. During the process of coating and drying, the coated surface is not allowed to contact any roller surfaces. The coating of only one surface of the substrate gives positive control of the resulting laminate.

When employing the Celgard films as the substrate, the films temporarily become transparent as the solvents penetrate and fill the micropores. The polymer is, however, of sufficiently high molecular weight, in the range of 5,000 $M_n$ such that it has mostly been excluded by the micropores. When the solvent is removed by evaporation and hot-air drying, a composite membrane is obtained having a thin, controlled, polysulfone-polydimethylsiloxane membrane residing thereon. The membrane is mechanically locked and bonded to the film, since sufficient lower molecular weight polymer is present to penetrate into the micropore openings to form such a mechanical bond. A coherent bonding is also obtained by the surface contact of the laminate components.

The process as described and as will be described allows continuous manufacturing of the desired material, and thickness of the membrane can be controlled by regulating such factors as casting solution concentrations, solvent mixtures and viscosity, and web speed and drying times.

A number of solvents may be used to form casting solutions but, the applicant has found that, care must be taken to choose solvent solutions which do not overly swell the substrate, cause phase separation in the block copolymer which is highly sensitive to microphase morphological changes, cause surface haze or which do not retard evaporation. Suitable solvents from which to draw a system formulation include: aromatic hydrocarbons such as benzene, toluene, xylene; ethers such as tetrahydrofuran; chlorinated hydrocarbons such as chlorobenzene, chloroform; esters such as ethyl acetate; alcohols, alkenes; nitroalkenes; ketones such as cyclohexanone; and aceto nitrile.

It is therefore an object of the invention to provide the method and apparatus for the continuous formation of laminates including an ultrathin polymer film and a substrate membrane.

It is a further object of the invention to provide a laminate formed by the solvent casting of a two phase siloxane-polyarylene polyether block copolymer onto a suitable microporous polypropylene film.

These and other objects of the invention will more fully appear from a consideration of the accompanying description, made in connection with the accompanying drawings in which the same indicia or numeral is utilized to identify the various elements throughout the several views.

DESCRIPTION OF A PREFERRED EMBODIMENT OF THE INVENTION

Figures 1, 2, 3:
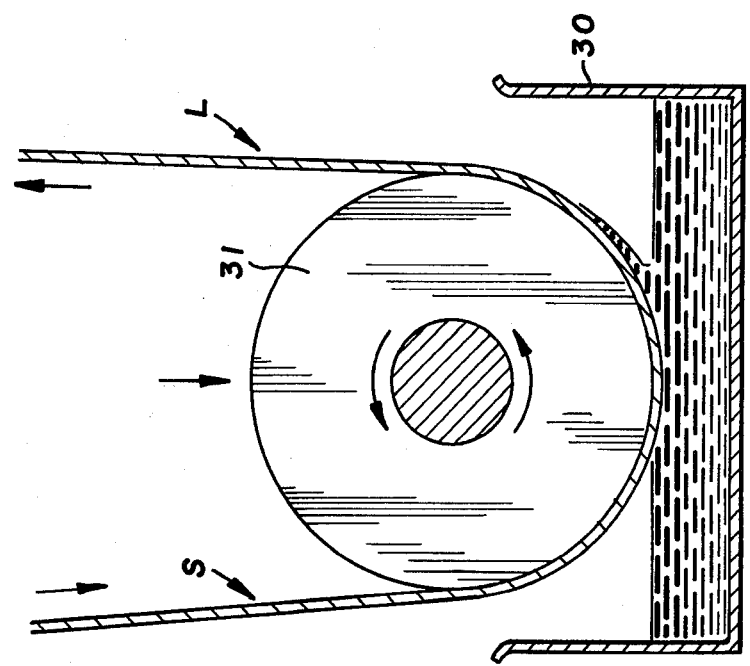
FIG. 1 is a schematic diagram of the apparatus provided for the continuous film coating process.
FIG. 2 is a schematic representation of the apparatus for performing the meniscus coating process; and, FIG. 3 is a typical cross section of the laminate resulting from the process.

In accordance with the objects and principals of the invention and the accompanying drawings, apparatus, generally designated 10, is provided for the continuous coating of a microporous substrate, and, in the form shown includes a feeding section 11, a meniscus dip, coating section 12, a drying section 13 and a take-up section 14. All of these sections are, in the form shown, mounted on a vertically oriented frame 15, and it is assumed that the frame is provided with sufficient supporting members and is of sufficient width to effectively support the various rollers illustrated thereon and to effectively carry a substrate of the desired width.

The feeding section includes a generally vertically arranged support standard 20 for rotatably receiving and mounting a supply roll of the selected substrate S thereon and a take-off arrangement consisting of three rollers 21, 22, 23 is provided for introductory control of the supplied substrate S. A tension mechanism is normally provided on the supply mounting roller 24 for proper feeding of the substrate S therefrom, and, in the form shown, the rollers 22, 23 may be, what is known in the industry as Mt. Hope Curved Rollers, or commonly termed "Bowed Rollers", the effect of such shaped rollers to maintain a centered and controlled flow or movement of sheet material along a path.

A vertically located roller provides a proper directional feed of the substrate web to the coating section 12 and an additional bowed roller 26 is provided intermediate roller 25 and the coating section 12 to again assist in web flow control.

The coating section 12, includes, in the form shown, a coating solution receptacle 30 with a web contacting roller 31 mounted vertically thereabove with a weight scale 32 being arranged directly therebelow and a pressurized solution supply 33 being provided for the introduction of the solvent solution into the receptacle 30 after the same has been passed through a final filter assembly 34. In order to prevent undesired evaporation of the solvent from the solution receptacle, shrouds, not shown, may be positioned in vertical relation to the receptacle.

The function of the scale is to allow monitoring of the level of the coating solution in the receptacle 30, by indication of the weight of the receptacle and contained solution.

The web of microporous substrate S is delivered to the coating station 12 and contact of one surface thereof with the solution is obtained and maintained through the web contacting or dip roller 31. The speed of the web through the coating section is a determining factor for the weight of the solution and therefore thickness of the coating being applied. The substrate S, in touching the surface of the liquid formulation, drags out and carries away a liquid film of the solution. Thickness of the liquid film depends primarily on the viscosity of the solution, the rate of the withdrawal of the substrate and the concentration of the copolymer in the solution. Increasing the web speed results in increasing the coating weight. Coating weight at a particular web speed increases as an exponential function of the solution viscosity.

The substrate S leaves the coating section 12 as a lamination L and is delivered to the drying section or station 13.

The drying section 13 includes a hot-air drying tunnel 35 with means being provided for the delivery of heated air thereto. This drying air must be particulate free and the drying temperature, length of drying tunnel 35 and web speed must be correlated to provide for proper drying.

After drying, the laminate is delivered through a plurality of rollers, such as bowed roller 36, idler roller 37 and an additional bowed roller 38 to a drive roller 39, which drive roller must be surfaced with material that will provide proper driving friction to the substrate side of the laminate. The web is delivered from the drive roller 39 to an additional bowed roller 40 and a subsequent spring loaded or gravity operable positioning roller device 41 to the take-up or collection roll 42. Obviously, this take-up roller must be properly controlled to properly take-up the delivered laminate.

It should be noted that the path of the laminate L is such that the coated side thereof does not come into contact with a roller surface.

Preferably, this entire operation should be accomplished under clean air conditions to prevent the entrapment of particles on the ultrathin film.

The apparatus for providing the laminate is relatively simple in nature and obvious controls and modifying devices such as speed and heat controls are necessary for the proper coating but, such controls and modifications are considered to be standard to any type of web moving, coating, drying and take-up devices for the continuous manufacture of materials and laminates.

The apparatus for manufacturing and the laminate resulting therefrom provides thin, uniform coatings of the polysulfone-polydimethylsiloxane copolymer to be applied evenly on one, and only one side of a microporous substrate. The use of this extremely smooth, blood compatible membrane offers additonal patient therapy benefits such as reduced damage to microcirculation, blood proteins, the complement system, formed elements of blood, as well as less hemolysis and neurogical effects compared to other membranes, membrane devices and bubbler type devices. Use of this polysulfone-polydimethylsiloxane membrane should also reduce, to a minimum, post operative complications such as hemorrhages, both interstitial and intra-alveolar, anemia and infections. Further, from usage benefits, unlike polyalkylsulfones and ordinary silicone rubber membranes this two phase block copolymer membrane is not tacky or sticky so that it may be easily handled and continuously manufactured and may easily be assembled into devices.

What is claimed is:
1. A laminate consisting of:
 a. a two phase block copolymer;
 b. a microporous substrate;
 c. said two phase block copolymer coating said substrate on only one side thereof; and, d. said microporous substrate having pores smaller than 5,000 angstroms.
2. The structure set forth in claim 1 and said two phase block copolymer being a two phase siloxanepolyarylene polyether block copolymer.
3. The structure set forth in claim 1 and said two phase block copolymer being a polysulfone-polydimethylsiloxane block copolymer.
4. The structure set forth in claim 3 and said microporous substrate being a polypropylene film.
5. The structure set forth in claim 3 and the molecular weights of the polysulfone-polydimethylsiloxane having a molecular range of weights from 1,500 to 100,000 $M_n$'s.
6. The structure set forth in claim 5 and said molecular weights being in the range of 10% to 90% siloxane and 90% to 10% polysulfone.
7. The structure set forth in claim 6 and the thickness of said block copolymer being in the range of 0.01 to 5.00 microns thick.
8. The structure set forth in claim 1 and said microporous substrate having pores in the range of 500 to 2,000 angstroms.
9. The structure set forth in claim 1 and the thickness of said substrate being in the range of 0.01 microns to 20 microns.
10. The structure set forth in claim 9 and the thickness of said substrate being in the range of 0.01 microns to 5 microns.

* * * * *